United States Patent
Moloney et al.

(10) Patent No.: US 12,048,806 B2
(45) Date of Patent: Jul. 30, 2024

(54) ELECTRONIC VAPOR PROVISION SYSTEM WITH AEROSOLIZABLE SUBSTRATE MATERIAL DISPENSING ARRANGEMENT

(71) Applicant: NICOVENTURES TRADING LIMITED, London (GB)

(72) Inventors: Patrick Moloney, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 805 days.

(21) Appl. No.: 17/057,549

(22) PCT Filed: May 21, 2019

(86) PCT No.: PCT/GB2019/051401
§ 371 (c)(1),
(2) Date: Nov. 20, 2020

(87) PCT Pub. No.: WO2019/224531
PCT Pub. Date: Nov. 28, 2019

(65) Prior Publication Data
US 2021/0212370 A1  Jul. 15, 2021

(30) Foreign Application Priority Data
May 23, 2018  (GB) ...................... 1808483

(51) Int. Cl.
*A24F 40/485* (2020.01)
*A24F 40/42* (2020.01)
(Continued)

(52) U.S. Cl.
CPC .............. *A61M 15/06* (2013.01); *A24F 40/42* (2020.01); *A24F 40/485* (2020.01); *A24F 40/10* (2020.01)

(58) Field of Classification Search
CPC ....... A61M 15/06; A24F 40/485; A24F 40/48; A24F 40/42; A24F 40/10
See application file for complete search history.

(56) References Cited

U.S. PATENT DOCUMENTS

| 5,894,841 A | 4/1999 | Voges |
| 10,918,133 B2 * | 2/2021 | Hon ........................ A24F 42/60 |
| (Continued) | | |

FOREIGN PATENT DOCUMENTS

| AU | 2019273754 A1 | 11/2020 |
| CN | 104254356 A | 12/2014 |
| (Continued) | | |

OTHER PUBLICATIONS

"Decision to Grant for Japanese Application No. 2020564596, mailed on Mar. 1, 2022", 5 pages.
(Continued)

*Primary Examiner* — Harshad C Patel
(74) *Attorney, Agent, or Firm* — Husch Blackwell LLP

(57) ABSTRACT

A component for a vapour provision system comprises a reservoir for storing aerosolisable substrate material, the reservoir bounded by a boundary wall with at least one movable section configured to move to reduce a storage volume of the reservoir; an outlet in the reservoir for dispensing aerosolisable substrate material from the reservoir; a one-way outlet valve at the outlet configured to open for the dispensing of the aerosolisable substrate material; and a dispensing arrangement operable to increase pressure of aerosolisable substrate material in an outlet volume of the reservoir which is not bounded by the movable section, so as to open the outlet valve and dispense a portion of aerosolisable substrate material, the subsequent absence of
(Continued)

Figure 1:
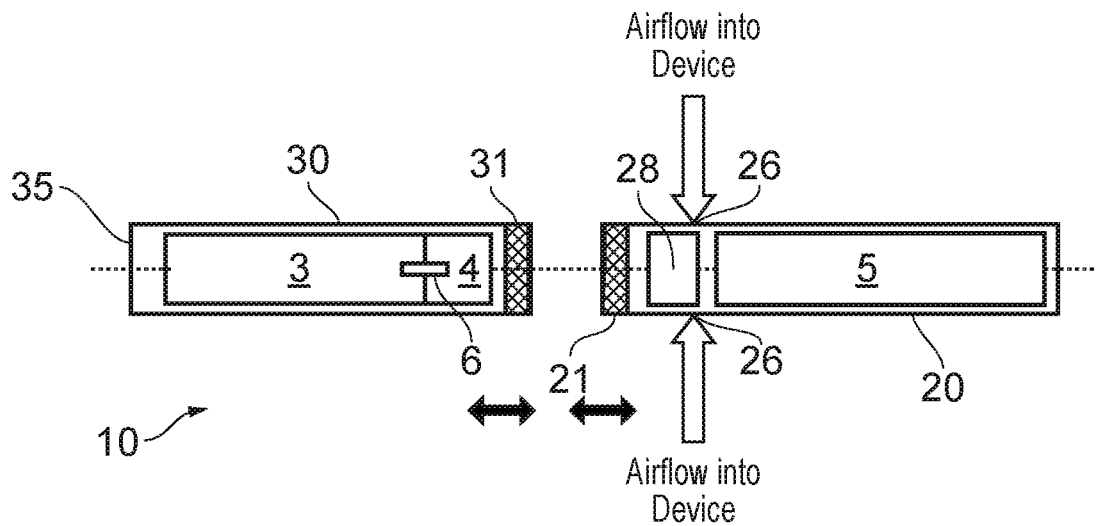

the dispensed portion reducing the pressure to allow the movable section of the boundary wall to move to reduce the storage volume.

20 Claims, 4 Drawing Sheets

(51) Int. Cl.
    *A61M 15/06*        (2006.01)
    *A24F 40/10*        (2020.01)

(56)           References Cited

U.S. PATENT DOCUMENTS

| | | | |
|---|---|---|---|
| 11,589,621 B2* | 2/2023 | Sur | A24F 40/65 |
| 2006/0196518 A1 | 9/2006 | Hon | |
| 2008/0257915 A1* | 10/2008 | Wold | A61M 11/007 |
| | | | 222/389 |
| 2015/0117842 A1* | 4/2015 | Brammer | F24H 1/0018 |
| | | | 392/394 |
| 2015/0272216 A1 | 10/2015 | Dai et al. | |
| 2016/0255876 A1 | 9/2016 | Rostami | |
| 2017/0071253 A1 | 3/2017 | Revell | |
| 2017/0071255 A1 | 3/2017 | Revell | |
| 2017/0280776 A1* | 10/2017 | Manca | H05B 3/44 |
| 2018/0154092 A1* | 6/2018 | Patoret | A24F 40/48 |

FOREIGN PATENT DOCUMENTS

| | | |
|---|---|---|
| CN | 105533811 A | 5/2016 |
| CN | 105848504 A | 8/2016 |
| CN | 105939625 A | 9/2016 |
| CN | 106998815 A | 8/2017 |
| CN | 107072321 A | 8/2017 |
| CN | 107690289 A | 2/2018 |
| EP | 3162229 A1 | 5/2017 |
| EP | 3232835 A1 | 10/2017 |
| JP | H08511966 A | 12/1996 |
| JP | 2006044710 A | 2/2006 |
| JP | 2014512207 A | 5/2014 |
| JP | 2017538409 A | 12/2017 |
| RU | 2336001 C2 | 10/2008 |
| WO | WO-2014037794 A2 | 3/2014 |
| WO | WO-2016096728 A1 | 6/2016 |
| WO | WO-2016198459 A1 | 12/2016 |
| WO | WO-2017045899 A1 | 3/2017 |
| WO | WO-2017108394 A1 | 6/2017 |
| WO | WO-2017220273 A1 | 12/2017 |
| WO | 2018037206 A1 | 3/2018 |

OTHER PUBLICATIONS

"International Preliminary Report on Patentability for Application No. PCT/GB2019/051401, completed on Oct. 8, 2020", 10 pages.
"International Search Report and Written Opinion received for PCT Patent Application No. PCT/GB2019/051401, mailed on Aug. 2, 2019", 11 pages.
"Office Action For Russian Application No. 2020137850, mailed on mailed on Jul. 2, 2021", 13 pages.
"Office Action received for Chinese Patent Application No. 2019800313149, mailed on Feb. 9, 2023", 13 pages.

* cited by examiner

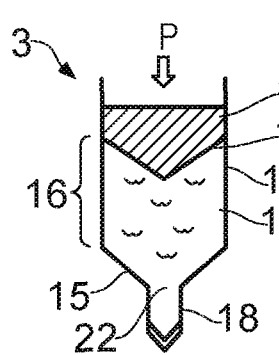  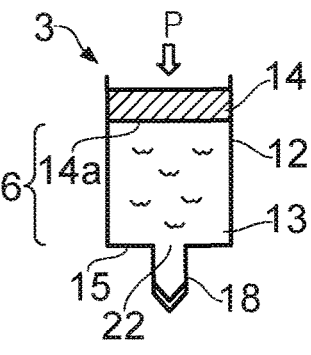 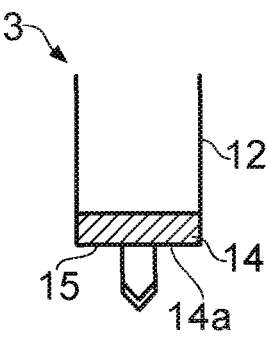
FIG. 3A  FIG. 3B  FIG. 3C  FIG. 3D
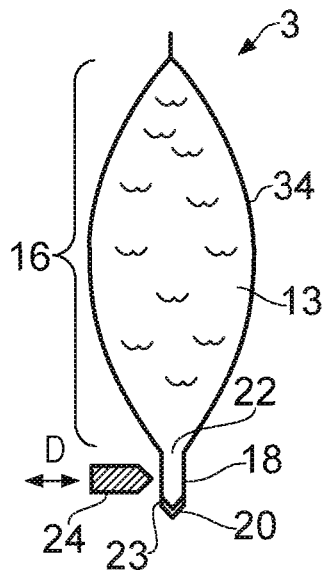 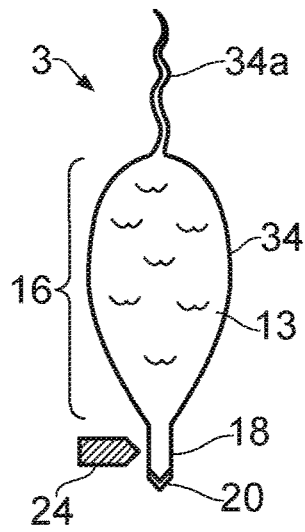 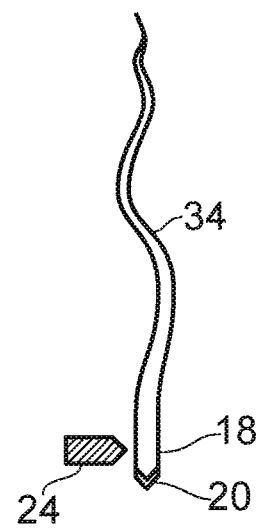
FIG. 4A  FIG. 4B  FIG. 4C
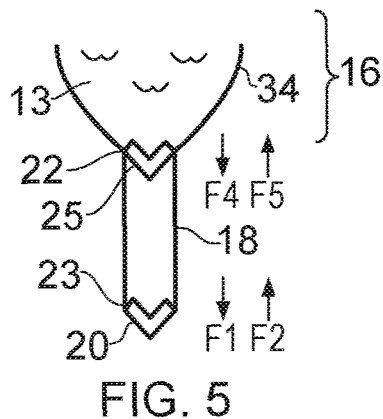
FIG. 5

ELECTRONIC VAPOR PROVISION SYSTEM WITH AEROSOLIZABLE SUBSTRATE MATERIAL DISPENSING ARRANGEMENT

PRIORITY CLAIM

The present application is a National Phase entry of PCT Application No. PCT/GB2019/051401, filed May 21, 2019, which claims priority from Great Britain Patent Application No. 1808483.0, filed May 23, 2018, each of which is hereby fully incorporated herein by reference.

TECHNICAL FIELD

The present disclosure relates to an electronic vapor provision system and components therefor which include arrangements for dispensing aerosolizable substrate material.

BACKGROUND

Many electronic vapor provision systems, such as e-cigarettes and other electronic nicotine delivery systems that deliver nicotine via vaporized liquids, and hybrid devices which additionally include a portion of tobacco or other flavor element through which vapor generated from a liquid is passed, include a reservoir that holds aerosolizable substrate material in a liquid or gel form. The substrate material is delivered from the reservoir to a vapor generating element, such as an electric heater, which operates to vaporize the substrate material and provide it as an aerosol for inhalation by a user of the system.

As the substrate material is consumed, it occupies a smaller proportion of the total storage volume available in the reservoir, and a volume of air (known as "headspace") develops to occupy the empty part of the reservoir and maintain a constant pressure within the reservoir, which is important to enable the continued emission of the substrate material from the reservoir. However, it is believed that the presence of headspace can contribute to leakage from a reservoir, in the form of emission of the substrate material at a greater rate than can be vaporized by the vapor generating element, and/or at times when the vapor generating element is not operational. Such leakage is undesirable since it wastes the substrate material, and can result in unwanted liquid droplets in the generated aerosol, and in the leakage of liquid both externally from the system which can soil the user, and within the system where it may damage electrical parts.

Accordingly, approaches intended to reduce such leakage are of interest.

SUMMARY

According to a first aspect of some embodiments described herein, there is provided a component for a vapor provision system, comprising: a reservoir for storing aerosolizable substrate material, the reservoir bounded by a boundary wall with at least one movable section configured to move to reduce a storage volume of the reservoir; an outlet in the reservoir for dispensing aerosolizable substrate material from the reservoir; a one-way outlet valve at the outlet configured to open for the dispensing of the aerosolizable substrate material; and a dispensing arrangement operable to increase pressure of aerosolizable substrate material in an outlet volume of the reservoir which is not bounded by the movable section, so as to open the outlet valve and dispense a portion of aerosolizable substrate material, the subsequent absence of the dispensed portion reducing the pressure to allow the movable section of the boundary wall to move to reduce the storage volume.

According to a second aspect of some embodiments described herein, there is provided an electronic vapor provision system comprising a component according to the first aspect.

According to a third aspect of some embodiments described herein, there is provided a reservoir installable into a vapor provision system and for storing aerosolizable substrate material, the reservoir comprising: a boundary wall defining a storage volume of the reservoir and having at least one movable section configured to reduce the storage volume; and an outlet volume in fluid communication with the storage volume, the outlet volume having an outlet for dispensing aerosolizable substrate material from the reservoir and a one-way outlet valve at the outlet configured to open for the dispensing of the aerosolizable substrate material; wherein the outlet volume is configured to cooperate with a dispensing arrangement in a vapor provision system when the reservoir is installed in the vapor provision system, the dispensing arrangement operable to increase pressure of aerosolizable substrate material in the outlet volume so as to open the outlet valve and dispense a portion of aerosolizable substrate material, the subsequent absence of the dispensed portion reducing the pressure to allow the movable section of the boundary wall to move to reduce the storage volume.

According to a fourth aspect of some embodiments described herein, there is provided a component for a vapor provision system, the component configured to receive a reservoir for storing aerosolizable substrate material that comprises a boundary wall defining a storage volume of the reservoir and having at least one movable section configured to reduce the storage volume, and an outlet volume in fluid communication with the storage volume, the outlet volume having an outlet for dispensing aerosolizable substrate material from the reservoir and a one-way outlet valve at the outlet configured to open for the dispensing of the aerosolizable substrate material; the component comprising a dispensing arrangement configured to cooperate with the outlet volume of a reservoir received by the vapor provision system, and operable to increase pressure of aerosolizable substrate material in the outlet volume so as to open the outlet valve and dispense a portion of aerosolizable substrate material, the subsequent absence of the dispensed portion reducing the pressure to allow the movable section of the boundary wall to move to reduce the storage volume.

According to a fifth aspect of some embodiments described herein, there is provided a component for an aerosol provision device comprising: a reservoir for storing aerosolizable substrate material, the reservoir bounded by a boundary wall with at least one movable section configured to move to reduce a storage volume of the reservoir, an outlet in the reservoir for dispensing aerosolizable substrate material from the reservoir; a one-way valve at the outlet configured to open to enable the dispensing of aerosolizable substrate material; and a dispensing element configured to removably apply a force to aerosolizable substrate material in a part of the storage volume not bounded by the movable section such that an application of force by the dispensing element pushes a portion of aerosolizable substrate material through the one-way valve and the outlet, and subsequent removal of the force allows the movable section of the boundary wall to move to reduce the storage volume in response to the absence of the dispensed portion of aerosolizable substrate material.

These and further aspects of the certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, a vapor provision system or part thereof including an aerosolizable substrate material dispensing arrangement may be provided in accordance with approaches described herein which includes any one or more of the various features described below as appropriate.

BRIEF DESCRIPTION OF THE DRAWINGS

Various embodiments of the invention will now be described in detail by way of example only with reference to the following drawings in which:

FIG. 1 shows a simplified cross-sectional schematic representation of an example vapor provision device in which aspects of the present disclosure may be implemented;

FIG. 2A shows a simplified cross-sectional schematic representation of a reducible volume reservoir with a liquid dispensing arrangement according to a first example;

FIGS. 2B, 2C and 2D show simplified cross-sectional schematic representations of examples of liquid dispensing arrangements;

FIGS. 3A and 3B show simplified cross-sectional schematic representations of an example reducible volume reservoir in a full and an empty state;

FIGS. 3C and 3D show simplified cross-sectional schematic representations of a further example reducible volume reservoir in a full and an empty state;

FIGS. 4A, 4B and 4C show simplified cross-sectional schematic representations of another example reducible volume reservoir with a liquid dispensing arrangement in a full state, a partially full state and an empty state;

FIG. 5 shows a simplified cross-sectional schematic representation of an example reducible volume reservoir outlet;

FIG. 6 shows a simplified cross-sectional schematic representation of a reducible volume reservoir outlet with a further example liquid dispensing arrangement;

FIG. 7 shows a simplified cross-sectional schematic representation of a reducible volume reservoir outlet with another example liquid dispensing arrangement; and FIGS. 8, 9 and 10 show simplified cross-sectional schematic representations of three example vapor provision devices comprising reducible volume reservoirs and liquid dispensing arrangements in accordance with the present disclosure.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. The disclosure is also applicable to systems configured to release compounds by heating, but not burning, a solid/gel substrate material. The substrate material may be for example tobacco or other non-tobacco products, which may or may not contain nicotine, which in some systems is provided in addition to liquid or gel substrate material so that the disclosure is also applicable to hybrid systems configured to generate aerosol by heating, but not burning, a combination of substrate materials. The substrate materials may comprise for example solid, liquid or gel which may or may not contain nicotine. A hybrid system may comprise a liquid or gel substrate and a solid substrate. The solid substrate may be for example tobacco or other non-tobacco products, which may or may not contain nicotine. The term "aerosolizable substrate material" as used herein is intended to refer to substrate materials which can form an aerosol, either through the application of heat or some other means. The term "aerosol" may be used interchangeably with "vapor".

As used herein, the term "component" is used to refer to a part, section, unit, module, assembly or similar of an electronic cigarette or similar device that incorporates several smaller parts or elements, often within an exterior housing or wall. An electronic cigarette may be formed or built from one or more such components, and the components may be removably or separably connectable to one another, or may be permanently joined together during manufacture to define the whole electronic cigarette. The present disclosure is applicable to (but not limited to) systems comprising two components separably connectable to one another and configured, for example, as an aerosolizable substrate material carrying component holding liquid or another aerosolizable substrate material, and a control unit having a battery for providing electrical power to an electrically operable element for generating vapor from the substrate material. For the sake of providing a concrete example, in the present disclosure, a cartomizer is described as an example of the aerosolizable substrate material carrying portion or component, but the disclosure is not limited in this regard and is applicable to any configuration of aerosolizable substrate material carrying portion or component. Also, such a component may include more or fewer parts than those included in the examples.

The present disclosure is particularly concerned with vapor provision systems and components thereof that utilize aerosolizable substrate material in the form of a liquid or a gel which is held in a reservoir, tank, container or other receptacle comprised in the system. An arrangement (configuration, mechanism, device, means and the like) for dispensing the substrate material from the reservoir for the purpose of delivering it for vapor/aerosol generation is included. The terms "liquid", "gel", "fluid", "source liquid", "source gel", "source fluid" and the like may be used interchangeably with "aerosolizable substrate material" and "substrate material" to refer to aerosolizable substrate material that has a form capable of being stored and dispensed in accordance with examples of the present disclosure.

FIG. 1 is a highly schematic diagram (not to scale) of an example aerosol/vapor provision system such as an e-cigarette 10. The e-cigarette 10 has a generally elongate shape, extending along a longitudinal axis indicated by a dashed line, and comprises two main components, namely a control or power component, section or unit 20 and a cartridge assembly or section 30, sometimes referred to as a cartomizer or clearomizer, and carrying aerosolizable substrate material and operating as a vapor-generating component.

The cartomizer 30 includes a reservoir 3 containing a source liquid or other aerosolizable substrate material comprising a formulation such as liquid or gel from which an aerosol is to be generated, for example containing nicotine. As an example, the source liquid may comprise around 1 to 3% nicotine and 50% glycerol, with the remainder comprising roughly equal measures of water and propylene glycol, and possibly also comprising other components, such as flavorings. Nicotine-free source liquid may also be used, such as to deliver flavoring. A solid substrate (not illustrated), such as a portion of tobacco or other flavor element through which vapor generated from the liquid is passed, may also be included. The reservoir 3 has the form of a storage tank, being a container or receptacle in which source liquid can be stored such that the liquid is free to move and flow within the confines of the tank. The reservoir 3 may be sealed after filling during manufacture so as to be disposable after the source liquid is consumed, or may have an inlet port or other opening through which new source liquid can be added. The cartomizer 30 also comprises an electrical heating element or heater 4 located externally of the reservoir tank 3 for generating the aerosol by vaporization of the source liquid by heating. A liquid transfer or delivery arrangement (liquid transport element) such as a wick or other porous element 6 may be provided to deliver source liquid from the reservoir 3 to the heater 4. A wick 6 may have one or more parts located inside the reservoir 3, or otherwise be in fluid communication with the liquid in the reservoir 3, so as to be able to absorb source liquid and transfer it by wicking or capillary action to other parts of the wick 6 that are in contact with the heater 4. This liquid is thereby heated and vaporized, to be replaced by new source liquid from the reservoir for transfer to the heater 4 by the wick 6. The wick may be thought of as a bridge, path or conduit between the reservoir 3 and the heater 4 that delivers or transfers liquid from the reservoir to the heater. Terms including conduit, liquid conduit, liquid transfer path, liquid delivery path, liquid transfer mechanism or element, and liquid delivery mechanism or element may all be used interchangeably herein to refer to a wick or corresponding component or structure.

A heater and wick (or similar) combination is sometimes referred to as an atomizer or atomizer assembly, and the reservoir with its source liquid plus the atomizer may be collectively referred to as an aerosol source. Other terminology may include a liquid delivery assembly or a liquid transfer assembly, where in the present context these terms may be used interchangeably to refer to a vapor-generating element (vapor generator) plus a wicking or similar component or structure (liquid transport element) that delivers or transfers liquid obtained from a reservoir to the vapor generator for vapor/aerosol generation. Various designs are possible, in which the parts may be differently arranged compared with the highly schematic representation of FIG. 1. For example, the wick 6 may be an entirely separate element from the heater 4, or the heater 4 may be configured to be porous and able to perform at least part of the wicking function directly (a metallic mesh, for example). Other means for vapor generation may be used in place of a heater, such as a vibrating vaporizer based on the piezoelectric effect, for example. In an electrical or electronic device, the vapor generating element may be an electrical heating element that operates by ohmic (Joule) heating or by inductive heating. In general, therefore, an atomizer can be considered to be a vapor-generating or vaporizing element able to generate vapor from source liquid delivered to it, and a liquid transport or delivery element able to deliver or transport liquid from a reservoir or similar liquid store to the vapor generator by a wicking action/capillary force. An atomizer is typically housed in a cartomizer component of a vapor generating system. In some designs, liquid may be dispensed from a reservoir directly onto a vapor generator with no need for a distinct wicking or capillary element. Embodiments of the disclosure are applicable to all and any such configurations which are consistent with the examples and description herein.

Returning to FIG. 1, the cartomizer 30 also includes a mouthpiece 35 having an opening or air outlet through which a user may inhale the aerosol generated by the heater 4.

The power component or control unit 20 includes a cell or battery 5 (referred to herein after as a battery, and which may be re-chargeable) to provide power for electrical components of the e-cigarette 10, in particular the heater 4. Additionally, there is a controller 28 such as a printed circuit board and/or other electronics or circuitry for generally controlling the e-cigarette. The control electronics/circuitry 28 connects the heater 4 to the battery 5 when vapor is required, for example in response to a signal from an air pressure sensor or air flow sensor (not shown) that detects an inhalation on the system 10 during which air enters through one or more air inlets 26 in the wall of the control unit 20. When the heating element 4 receives power from the battery 5, the heating element 4 vaporizes source liquid delivered from the reservoir 3 by the liquid delivery element 6 to generate the aerosol, and this is then inhaled by a user through the opening in the mouthpiece 35. The aerosol is carried from the aerosol source to the mouthpiece 35 along an air channel (not shown) that connects the air inlet 26 to the aerosol source to the air outlet when a user inhales on the mouthpiece 35.

The control unit (power section) 20 and the cartomizer (cartridge assembly) 30 are separate connectable parts detachable from one another by separation in a direction parallel to the longitudinal axis, as indicated by the solid arrows in FIG. 1. The components 20, 30 are joined together when the device 10 is in use by cooperating engagement elements 21, 31 (for example, a screw or bayonet fitting) which provide mechanical and electrical connectivity between the power section 20 and the cartridge assembly 30. This is merely an example arrangement, however, and the various parts and features may be differently distributed between the power section 20 and the cartridge assembly section 30, and other components and elements may be included. The two sections may connect together end-to-end in a longitudinal configuration as in FIG. 1, or in a different configuration such as a parallel, side-by-side arrangement. The system may or may not be generally cylindrical and/or have a generally longitudinal shape. Either or both sections or components may be intended to be disposed of and replaced when exhausted (the reservoir is empty or the battery is flat, for example), or be intended for multiple uses enabled by actions such as refilling the reservoir and recharging the battery. In other examples, the system 10 may be unitary, in that the parts of the control unit 20 and the cartomizer 30 are comprised in a single housing and cannot be separated. Embodiments and examples of the present disclosure are applicable to any of these configurations and other configurations of which the skilled person will be aware.

During use of a system such as the electronic cigarette of FIG. 1, the source liquid gradually flows or is drawn out of the reservoir and is consumed by the atomizer to generate the required aerosol stream for inhalation. The reservoir is not arranged to be airtight, and consequently, air is drawn into the reservoir to replace the source liquid as it is removed for consumption, so as to preserve a constant pressure in the reservoir and enable the continued emission of the source liquid to the atomizer. This air forms a gradually increasing volume known as the headspace, and it is recognized that the presence of a headspace can contribute to leakage of source liquid from the reservoir. The leakage can comprise an egress of an excessive amount of source liquid via the intended liquid delivery route from the reservoir to the vapor generator, so that the vapor generator is unable to process all the source liquid it receives and unvaporized source liquid is released within the system. This can arise from changes in environmental pressure or shocks to the system (such as if it is dropped) which produce a change in volume of the headspace or a pressure wave in the headspace that pushes source liquid out of the reservoir.

The present disclosure proposes to address these issues by configuring a reservoir that functions with little or no headspace. This is enabled by providing a reservoir with a reducible volume, so that the storage capacity of the reservoir is reduced in line with the source liquid consumption, keeping the available storage volume matched or nearly matched to the remaining volume of liquid so that less or no air enters the reservoir and no headspace forms. The reducible volume is enabled by a reservoir defined by a wall with at least one movable section that can move inwardly to reduce the volume. Source liquid is dispensed according to vapor generating requirements, and after dispensing, the remaining reduced quantity of source liquid produces a lower pressure inside the reservoir. This lower pressure causes the movable section of the wall to move inwards and equalize the pressures inside and outside the reservoir. The dispensing of the liquid is achieved by application of a force to a volume liquid in the reservoir which is remote from the movable wall section and proximate to an outlet of the reservoir. The applied force pushes a portion of liquid out through the outlet, and when the force is removed, the lower fluid pressure in the vicinity of the outlet is communicated to the liquid remaining in the bulk of the reservoir, to pull in the movable section. The reservoir storage volume or capacity is thereby reduced in response to the dispensing of liquid from the reservoir, and the decreasing quantity of liquid remaining in the reservoir pulls the reservoir boundary wall inwardly around it to inhibit formation of a headspace.

FIG. 2A shows a schematic longitudinal cross-sectional representation of a first example arrangement of a reducible volume reservoir with a liquid dispensing arrangement. The reservoir 3 is substantially cylindrical, and comprises an outer cylindrical wall 12 within which is received a movable plunger or piston 14 which fits tightly inside the cylindrical wall 12 to create a fluid-tight or near fluid-tight seal against the wall 12, but which is able to slide up and down within the cylindrical space bounded by the wall 12. The cylindrical wall 12 and the plunger 14 together act as a boundary wall to define a storage volume 16 of the reservoir 3, within which a fluid form of aerosolizable substrate material (source liquid) 13 is stored. Sliding movement of the plunger 14 changes the size of the storage volume 16, with an inward (downward) movement in the direction P acting to reduce the storage volume. The plunger 14 provides a movable section or portion of the overall boundary wall of the reservoir 3, defined by the wall 12 combined with the plunger 14. The cylindrical wall 12 and the plunger 14 may have a configuration similar to a barrel and plunger of a syringe, for example. Shapes other than cylindrical may be used to embody the reservoir 3, however. The cylindrical wall 12 may be formed from a rigid or semi-rigid material such as a plastics material, for example. The material may be opaque or transparent, where a transparent material may be useful in systems that allow the user visual access to the reservoir so that a remaining amount of liquid can be observed. It may be formed by molding in one or more pieces, for example.

The reservoir 3 also comprises an outlet volume 18 which is in fluid communication 22 with the storage volume 16 and leads to an outlet 23 through which the source liquid 13 can exit the reservoir, to allow dispensing of the source liquid 13 from the reservoir 3. In this example, the outlet volume 18 has the shape of a tube or pipe leading from the storage volume 16, and joined to the cylindrical wall 12 by a tapered portion 15 which provides a lower wall of the storage volume 16 opposite to the movable wall provided by the plunger 14, and also has the effect of reducing the diameter (bore) of the reservoir from a larger diameter for the storage volume 12 to a narrow diameter for the outlet tube 18. The outlet 23 of the outlet volume 18 is provided with an outlet valve 20. This is a one-way valve which can open under a sufficient applied pressure or force (cracking pressure) to let liquid pass from the outlet volume 18 through the opening 23, but otherwise remains closed, and does not let fluid including air into the reservoir 3. In steady state conditions, the reservoir 3 is a closed, substantially fluid-tight volume created by the cylindrical wall 12, the movable wall portion 14, the tapered wall 15, the outlet tube 18 and the closed outlet valve 20. The outlet tube 18 may be formed integrally with the cylindrical wall 12, or may be formed separately and joined together such as by gluing or welding. A unitary construction may be preferred to reduce the risk of leakage through any poorly made joints, but a non-unitary construction allows different materials to be used to provide the storage volume and the outlet volume.

A dispensing arrangement or element (dispenser) 24 is provided adjacent to the outlet tube 18. The purpose of the dispensing arrangement 24 is to apply a force to liquid in the outlet volume so as to increase the pressure of the liquid sufficiently to overcome the cracking pressure of the outlet valve 10. Hence, it can be considered as a force applicator or a pressurizer. In this example, the dispensing arrangement 24 is configured as a pinching or pincer mechanism, or constrictor, which can be moved inwardly in the direction D towards the side of the outlet tube 18 so as to press against or squeeze the tube 18. This distorts or deforms the wall of the tube 18 inwardly so as to decrease the outlet volume and hence increase the pressure of the liquid in the outlet volume 18 and apply a force to the outlet valve 20, by increasing the fluid pressure acting on it. The outlet tube 18 is therefore made of an elastically resilient material such as rubber or another elastomeric material so that the required force can be transferred from the dispenser 24 to the liquid via inward distortion of the wall of the outlet tube. The dispenser 24 can comprise any solid or substantially rigid element or member mounted for movement towards and away from the tube 18, such as via a motor and linear drive mechanism (worm drive or lead screw).

When the electronic cigarette is activated for the generation of aerosol, the apparatus of FIG. 2A operates as follows. The dispenser 24 is operated to move inwardly and constrict the outlet tube 18, so as to apply a force to the liquid in the outlet volume, which is liquid proximate to the outlet valve 20 and remote from the movable portion 14 of the boundary wall of the reservoir 12. The force increases the pressure in the liquid in the locality of the outlet valve 20 to a level which exceeds the cracking pressure of the outlet valve 20 and causes the outlet valve 20 to open. A portion or droplet of liquid 32 is expelled or dispensed through the outlet 23 of the reservoir 12 via the open valve 20. The dispensed portion 32 is effectively pushed out of the reservoir by the applied force delivered from the dispensing arrangement 24 squeezing the outlet tube 18.

Figure 2A:
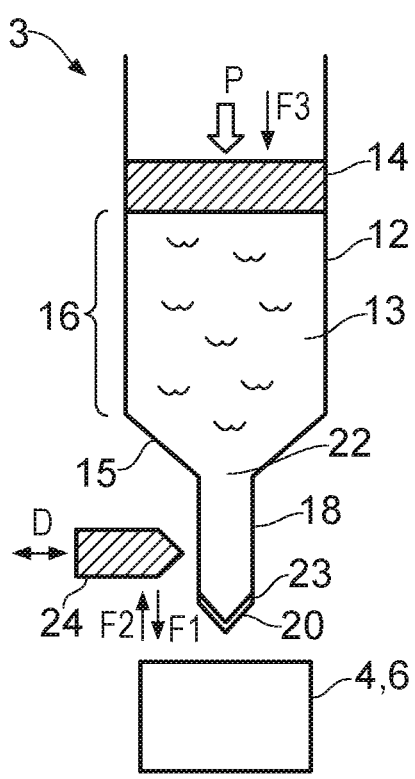
Figure 2B:
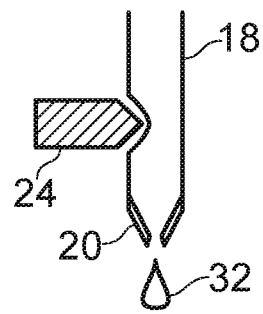
Figure 2C:
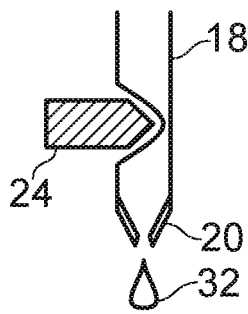

FIG. 2B depicts this situation, with the portion of liquid 32 leaving the reservoir through the open valve 20 while the tube 18 is constricted by the dispenser 24. Once the expelled portion of liquid 32 has been dispensed and is no longer contained within the outlet volume of the reservoir 3, the pressure near the valve 20 is reduced below the cracking pressure and the valve 20 resumes its closed position. The dispensing arrangement 24 can then be moved outwardly along the direction D to remove the squeezing effect from the outlet tube 18, which is free to resume its undeformed shape. The overall volume of the reservoir 3, being the storage volume 12 plus the outlet volume 18 is restored to its previous size, prior to the dispensing of the droplet 32. However, the removal of the dispensed droplet 32 has decreased the amount of liquid available to occupy that volume, and the liquid pressure in the volume is decreased compared to before the droplet 32 was dispensed. The local liquid pressure reduction near the outlet valve 20 that allowed the valve 20 to close behind the dispensed droplet 32 is communicated throughout the liquid via the fluid communication 22 between the outlet volume 18 and the storage volume 12. The lowered pressure inside the reservoir 3, together with the atmospheric pressure acting on the external side of the plunger 14 (i.e. the side outside the storage volume), acts to pull the movable wall provided by the plunger 14 inwardly in the direction P until the pressure inside the reservoir is restored to equilibrium with the atmospheric pressure outside the reservoir. Hence, the overall volume of the reservoir 3 is reduced by enabling a reduction of the storage volume 12 in response to the dispensing of a portion of source liquid 32, and the formation of a headspace within the reservoir is prevented (or at least inhibited in the event that the reservoir is not fully air-tight). The reservoir volume is reduced in use to correspond to the remaining volume of liquid held in the reservoir.

The outlet 23 of the reservoir 3 is located to provide the dispensed portion of liquid 32 to the atomizer 4, 6 for vaporization. Depending on the configuration of the atomizer, the liquid droplet 32 may be delivered onto or into a wicking element or other liquid transport element such as a capillary channel, which is arranged to carry liquid to a heater or other vapor generator. In other arrangements, the liquid droplet 32 is delivered directly to the heater or other vapor generator, and no liquid transport element is required. The disclosure is not limited in this regard.

In the example of FIG. 2B, the dispensing arrangement produces only a partial constriction or narrowing of the outlet tube 18; this minor distortion of the tube 18 is sufficient to increase the pressure enough to open the outlet valve 20. The tube 18 itself is not fully closed, but the dimensions of the outlet tube and the aperture of the opened valve are small so that capillary forces prevent a continuing flow of liquid past the constriction and out through the open valve once the initial portion of liquid 32 has been dispensed.

FIG. 2C shows an alternative example in which the dispensing arrangement 24 is configured to squeeze the outlet tube sufficiently so as to close it by bringing opposite sides of the tube wall into contact, and liquid flow along the tube 18 towards the outlet 23 is fully restricted. The tube width and the valve aperture can be sized to allow all liquid in the outlet tube which is downstream of the pinching location for the dispenser 24 to flow through the open valve 20 to create the dispensed portion of liquid 32. In other words, capillary forces do not retain liquid inside the tube, and the closure of the tube by the dispenser in its inward position acts to retain the remainder of the liquid inside the reservoir when the valve is open. The valve 20 can close once the liquid droplet 32 has been dispensed and there is no more pressurized liquid adjacent to the valve 20 to overcome the cracking pressure.

The dispenser 24 can thereby act as a seal to close the reservoir 3, and aid in the minimization of leakage. To utilize this function, the dispenser 24 may have a default position in which it constricts the outlet tube to close the bore of the tube and prevent liquid flow, as in FIG. 2C. This position is maintained when no liquid is required by the atomizer. Then, when vapor generation is required, the dispenser 24 is moved outwardly, away from the outlet tube 18 (to the position in FIG. 2A), to release the pinching action and open the bore of the tube. This increases the overall reservoir volume, reduces the liquid pressure, and draws the plunger inwardly to a new reduced reservoir volume, allowing liquid to move along the outlet tube to the outlet valve 20. Then, the dispenser is moved inwardly back to the default position to squeeze the tube 18 closed, apply a force to the liquid in the outlet volume and increase the liquid pressure to open the valve 20. The liquid droplet 32 is dispensed through the open valve 20, which closes afterwards. In summary, the dispensing of the liquid droplet is effected by moving the pinching mechanism of the dispenser from a default restricting position to an open position and back to the default position. While the default restricting position usefully completely closes the outlet tube to seal the reservoir, this is not essential, and a partial restriction may suffice. These arrangements are in contrast to the previously described operation in which dispensing is effected by moving the pinching mechanism of the dispenser from a default open position where the outlet tube is undistorted and unrestricted, to a restricting position to squeeze the outlet tube, and back to the default open position.

In either of these operational configurations, the various parts are implemented so that a pressure F1 (see FIG. 2A) required to open the one-way valve is smaller than a pressure F3 required to move the plunger (by the sliding action inside the cylindrical wall). Further, the pressure F3 required to move the plunger is smaller than a pressure F2 required to overcome the one-way valve and cause it to open in the "wrong direction" (i.e. by a pressure acting externally towards the inside the reservoir). In this way, the appropriate pressures cooperate following action of the dispensing arrangement, so as to expel the liquid droplet and cause the reduction in the reservoir volume, without letting any suction of air or liquid through the valve into the reservoir. Overall, $F1<F3<F2$.

Considered in the terminology of the technical field of pumps, this arrangement would be referred to as a positive displacement pump.

The reservoir should be housed in a non-airtight environment (within some housing or casing of the e-cigarette, or forming part of the exterior wall of the e-cigarette) to enable the equalization of pressures inside and outside the reservoir which causes the inward movement of the movable portion of the reservoir boundary wall (the plunger in the examples thus far).

Figure 2D:
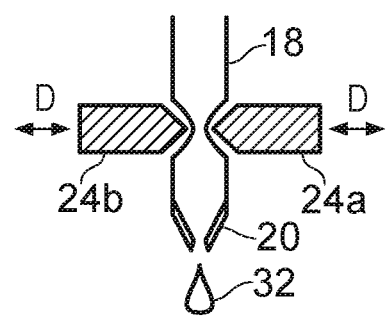

FIG. 2D shows a further example in which the squeezing or pinching of the outlet tube 18 to reduce or restrict its bore is effected by inward urging from two opposites side of the outlet tube 18, using two movable elements 24a, 24b that can move inwardly towards one another to pinch or close the tube 18 positioned between them, and outwardly away from each other to release or open the tube 18. The elements 24a, 24b might be two individual elements each moved by a separate linear drive. An alternative arrangement might be two elements or arms coupled by a hinge so as to be able to open and close like pincers or callipers, where the opening and closing motions are controlled by a drive mechanism. A spring might be used to bias the elements in either the open or closed position (depending on whether the default position for the dispenser is an open position or a pinching, restricting position), so that the drive mechanism need only effect movement in one direction. Both arms of the pincer arrangement may be movable, or one may be fixed while the other is movable towards and away from the other.

In other examples, the dispensing arrangement might be a collar that fully encircles the outlet tube and is able to be contracted to decrease its circumference and restrict the bore of the tube, and expanded to increase its circumference to open the bore of the tube.

Other configurations for effecting the movement of members or elements that urge against one or more sides of the outlet tube to deform it and exert a force on the liquid inside will be apparent to the skilled person. Another example is the use of one or more piezoelectric elements able to expand and reduce in size under an applied voltage, so as to move against and away from the tube wall. Alternative designs which lack any urging members movable against and away from the outlet tube are also possible. For example, the tube may be gripped by or otherwise secured to a holding member so that a torque can be applied to it to effect a twisting motion in a plane substantially orthogonal to the longitudinal axis of the tube, to distort the side walls of the tube and produce a restriction in the bore size and increased pressure on the liquid inside.

An attractive feature of a reservoir with a reducible volume is that, if the volume can be reduced substantially to nothing, all or almost all of the liquid can be expelled from the reservoir and made available for vaporization. This can reduce waste compared to configurations such as those that rely on a wick to draw liquid from a reservoir, where liquid caught in regions away from the wick cannot be extracted. In examples of the present disclosure which utilize a movable wall in the form of a plunger, such as the FIG. 2A example, a zero or near-zero volume can be achieved if the plunger is arranged to move towards the outlet volume of the reservoir, as in FIG. 2A, and can also be brought as closely as possible towards the boundary wall of the reservoir where the fluid communication between the storage volume and the outlet volume is located. In the FIG. 1 example, the plunger 14 can only move as far as the base of the cylindrical wall 12, and a small conical volume remains between the underside of the plunger 14 and the tapered wall.

FIG. 3A shows an alternative configuration which allows the storage volume 16 to be reduced effectively to zero by inward movement of the plunger 14. The underside 14a of the plunger 14, in other words, the surface of the plunger facing the interior of the storage volume 16, is shaped to correspond with the inwardly facing surface of the opposing wall as the base of the reservoir 3, in which the fluid communication 22 to the outlet volume 18 is defined. As in FIG. 2A, this wall 15 is a tapered wall, and consequently, the underside 14a of the plunger 14 has a matching conical shape with the same angle of slope as the tapered wall. This allows the plunger 14 to be pulled into close contact with the tapered wall 15 as liquid is expelled from the reservoir 3, leading to total elimination of the storage volume 16 as shown in FIG. 3B.

FIGS. 3C and 3D show a further example intended to enable a zero volume storage volume to be achieved, in which the underside 14a of the plunger 14 is flat (planar) and orthogonal to the direction of movement P, and the wall 15 forming the base of the storage volume 16 is also flat, in a parallel plane. Hence, the two surfaces can be brought into contact as shown in FIG. 3D. Any other matching or cooperating shapes for the plunger underside 14a and the base wall 15 can be used to achieve this effect. Note that other parts of the apparatus are omitted from FIGS. 3A to 3D for the sake of clarity.

In other examples, the facility to reduce the volume of the reservoir is effected by use of a collapsible receptacle, in place of a sliding wall or plunger as in the FIGS. 2A to 3D examples.

FIG. 4A shows a simplified cross-sectional view of an example configuration implemented with a collapsible receptacle. The bulk of the reservoir 3 is embodied by a receptacle in the form of a pouch or bag 34 formed from a flexible waterproof material such a thin plastics material such as polyethylene or a metallized polymer film (foiled polymer), or rubber. Thermoform plastics and other materials that can be thermally fused (to seal edge seams of the pouch, and connect the outlet valve, for example) are useful; these include polyethylene terephthalate (PET), polypropylene (PP), polyethylene (PE), low-density polyethylene (LDPE), polyvinyl chloride (PVC), thermoplastic olefin (TPO), polyethylene terephthalate glycol-modified (PETG), ethylene vinyl acetate (EVA), epoxide (EP) and polyurethane (PU). Other materials are not excluded, however. The reservoir should be able to deflate, but preferably should not apply significant pressure to its contents. Receptacles of the type commonly known as doypacks and pillow pouches are suitable, for example. The pouch 34 forms the boundary wall of the reservoir 3 to define the storage volume 16 of the reservoir 3, and is closed (sealed) except for an opening where it is in fluid communication 22 with the outlet volume 18 which is again configured as an outlet tube. The outlet tube 18 provides the outlet 23 of the reservoir, and is provided with a one-way valve 20 through which liquid can be dispensed, as before. Also as before, a dispensing arrangement 24 is provided adjacent the outlet tube 18 to urge against the side wall of the tube 18 and deliver a force to liquid in the tube.

In FIG. 4A, the pouch 34 is filled with liquid, following manufacture (or possibly following refilling by the user, if a suitable filling port is provided (not shown)). As with the previous examples, operation of the dispensing arrangement 24 presses or squeezes the outlet tube 18 to pressurize the liquid in the outlet volume, proximate to the outlet 23, sufficiently to overcome the cracking pressure of the valve so that the valve 20 opens and dispenses a portion of liquid. Retraction of the dispensing arrangement 24 away from the outlet tube 18 releases the pressure so that the tube 18 resumes its previous shape, causing a pressure drop in the liquid in the outlet volume which is communicated via the fluid communication 22 to the storage volume. This reduced pressure inside the reservoir causes the wall of the pouch 34 to be pulled inwardly to reduce the storage volume 16 available for holding the liquid 13, and equalize pressure in the reservoir with the external pressure. Note that the dispensing arrangement may alternatively operate in the opposite mode described with reference to FIG. 2C, in which the squeezing position is the default.

FIG. 4B shows the state of the reservoir after a number of dispensing operations, when about half the liquid 13 in the reservoir has been consumed. The upper part 34a of the pouch 34, remote from the outlet volume 18, has collapsed by the walls of the pouch 34 being pulled towards each other and eventually into contact. The size of the storage volume 16 has been reduced by about half, to match the amount of remaining liquid 13 in the reservoir 3.

FIG. 4C shows the eventual state of the reservoir 3 when all or most of the liquid has been dispensed. The pouch 34 is fully collapsed (the opposite walls of the pouch have been sucked against one another by the pressure equalizations following each dispensing action over the full extent of the pouch 34), reducing the storage volume substantially to zero.

FIG. 5 shows a cross-sectional view of the outlet volume of an alternative configuration including a collapsible pouch. In addition to the parts shown in FIG. 4A, the reservoir includes a second one-way valve 25 that separates the storage volume 16 from the outlet volume 18. In this example the second one-way valve 25 is located at the junction between the storage volume 16 and the outlet volume 18, where the pouch 34 is connected to the outlet tube 18, and the two volumes are in fluid communication 22. Opening of the second valve 25 is in a flow direction from the storage volume 16 into the outlet volume 18. The outlet valve 20 can be considered as a distal valve since it is at the end of the outlet tube 18 remote from the storage volume 16, and the second valve 25 at the fluid communication junction 22 can be considered as a proximal valve.

In operation, the dispensing apparatus (not shown in FIG. 5, for simplicity) acts on the outlet tube 18 to increase the pressure inside as previously described. This overcomes the cracking pressure of the outlet valve (distal valve) 20, which opens to dispense a portion of liquid. When the dispensing apparatus is deactivated, or withdrawn from contact with the outlet tube 18, the outlet tube resumes its rest configuration (an undistorted shape with the full outlet volume). This increase in the outlet volume decreases the liquid pressure in the outlet tube (since the volume of the dispensed portion is now missing). The reduced pressure in the outlet tube 18 falls below the liquid pressure in the storage volume. Hence, there is a greater pressure on the proximal side of the proximal valve 25 (the storage volume side), which overcomes the cracking pressure of the proximal valve 25 and causes it to open. Liquid is drawn through the open proximal valve 25 from the storage volume 16 to the outlet volume 18 owing to the pressure difference. The pressure in the storage volume 16 then drops owing to the reduced amount of liquid in the storage volume, and this reduced pressure can no longer keep the proximal valve 25 open, so it shuts. The reduced pressure also causes the pouch walls to be pulled inwardly, collapsing the pouch 34 slightly until the pressures inside and outside the storage volume 16 are equalized. The storage volume 16 is thus reduced, without the creation of any headspace in the reservoir 3.

To achieve the appropriate operation, and prevent liquid or air being drawn the wrong way through the valves 20, 25, the valves are each selected to have appropriate operating forces or pressures. The pressure F1 required to open the distal valve 20 and dispense a portion of liquid is smaller than the pressure F5 required to incorrectly open the proximal valve 25 (i.e. to open it for flow in the direction into the storage volume). In this way, pressure changes in the outlet volume 18 cannot cause the proximal valve 25 to open preferentially over the distal valve 20, ensuring the liquid in the outlet volume 18 is dispensed from the outlet 23 rather than being pushed back into the storage volume when the dispensing arrangement acts to increase the pressure in the outlet volume 18. Also, the pressure F4 required to open the proximal valve 25 is less than the pressure F2 required to incorrectly open the distal valve 20 (i.e. to open it for flow in the direction into the outlet volume). This ensures that the outlet volume is replenished from the storage volume via the proximal valve after a portion of liquid has been dispensed, without risk of the outlet valve 20 opening to suck in air or liquid from outside. So, F1<F5 and F4<F2.

The inclusion of a second one-way valve acts to partially isolate the outlet volume 18 from the storage volume 16. When the dispensing arrangement 24 acts on the outlet tube 18, the applied force is confined to the smaller volume of liquid in the outlet tube 18, rather than being applied to the total body of liquid in the entire reservoir. This allows the required pressure increase for opening the distal valve 20 to be achieved for a smaller applied force (smaller distortion of the tube, for example), so the dispensing arrangement 24 can be implemented more simply, and the action of the dispensing arrangement 24 on the outlet tube can be less extreme, reducing the risk of damage being caused to the outlet tube. A second valve located between the outlet volume and the storage volume can be implemented with any design of reservoir, and is not limited to the collapsible container examples of FIGS. 4A to 4C.

The collapsible container (bag or pouch) may be made of a material which is potentially vulnerable to accidental damage, since it should be sufficiently flexible to respond easily to the pressure changes that cause it to collapse, and this may be achieved more readily if the material is thin. Accordingly, the e-cigarette may be designed so that the collapsible reservoir is housed within a rigid or semi-rigid outer container or housing when it is installed for use in the e-cigarette. The outer housing will afford a degree of protection against damage to the pouch. However, it should not be air-tight, so that atmospheric pressure can be maintained around the pouch to cause it to collapse when liquid is dispensed. The outer housing may be a solid wall, or could be wholly or partly perforated, including a grill or mesh structure.

Examples have been given of dispensing arrangements comprising one or more movable parts that physically interact with the outlet tube to distort its walls and hence reduce its volume to cause a pressure increase for the liquid inside. These examples typically comprise a mechanical assembly configured to exert a force on the outlet tube so as to squeeze or constrict it. The outlet tube should be made from a suitably resilient material that can withstand repeated interactions with the mechanical assembly without damage, at least for the expected lifetime of the reservoir. The reservoir may be intended as disposable once the liquid has been consumed, or it may be able to be refilled by the user, if the design permits the storage volume to be restored to its original size. In other designs, the outlet tube may be considered as part of the dispensing arrangement, and the user can connect a reservoir to it via a coupling or engaging mechanism (such as a screw thread or a friction-based push fit) at the fluid communication location between the storage volume and the outlet volume. In such a case, the reservoir can include a breachable seal that is ruptured by the engagement to the outlet tube, so that the connection can be made without spillage of the liquid from the storage volume.

However, the disclosure is not limited in this way, and other configurations of dispensing arrangement may be used. Overall, the dispensing arrangement functions to increase the pressure in the liquid in the vicinity of the outlet valve so as to achieve the cracking pressure and enable outward flow of the liquid through the outlet valve, and any convenient arrangement that enables this can be used.

Piezoelectric elements have been mentioned already as a way to implement a dispensing arrangement operating via a pinching effect; the piezoelectric effect can be used to provide the advance and retraction of elements that engage with the outlet tube (where the elements may be piezoelectric material, or may be coupled to the piezoelectric material). The piezoelectric effect might be used differently to produce the pressure increase, however. A piezoelectric element (or more than one) can be arranged adjacently to the outlet tube so that when the element is caused to rapidly and momentarily expand or otherwise change shape by application of a suitable actuating voltage, the dimensional change causes it to strike against the outlet tube and generate a pressure wave in the liquid inside the tube. This temporarily increases the liquid pressure adjacent to the outlet valve, which opens under the cracking pressure and dispenses a portion of liquid. Any other configuration that enables a striking or hammering element to be moved rapidly and forcefully enough to impact the outlet tube hard enough to induce the required pressure wave may also be used. This arrangement does not require that the material of the tube be elastically deformable as in the squeezed arrangements; rather, the material should be able to withstand the repeated impacts. Thus, a further range of materials is made available for use. For example, the outlet tube can be formed integrally with the cylindrical side wall of the reservoir's storage volume in the FIG. 2A example, from a substantially rigid material.

Figure 6:
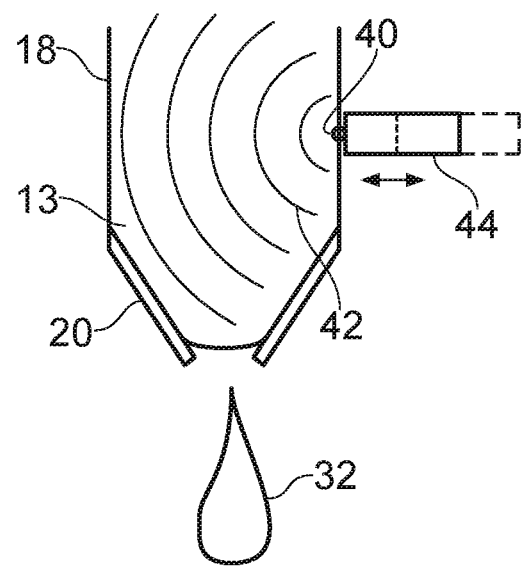

FIG. 6 shows a simplified cross-sectional view of an example utilizing a pressure wave to effect the droplet dispensing. As before, the reservoir terminates in an outlet volume embodied as an outlet tube 18, with a one-way outlet valve 20 at its lower end remote from the storage volume of the reservoir (not shown). A dispensing arrangement in the form of a striking element 44 is located next to the side wall of the tube 18, and is able to rapidly move from a rest position (shown in phantom) to an impact position (solid outline) and back to the rest position, for example actuated via the piezoelectric effect. The movement between the two positions may be movement of the entire striking element, as depicted, or may be movement of the front, striking surface only if the piezoelectric effect provides a sufficient expansion in size. In the impact position, the striking element strikes against the wall of the tube 18 at an impact location 40, and the force of the blow is transmitted through the material of the wall and into the liquid 13 inside the tube 18 where it propagates as a pressure wave 42. The pressure wave 42 increases the liquid pressure at the outlet valve 20 to cause the valve 20 to open, and a portion 32 of liquid is dispensed. More than one striking element 44 may be used as desired.

It should be appreciated that other ways of forming a pressure wave to effect the droplet dispensing may be used instead and are within the scope of the present disclosure. For instance, the pressure wave may be an acoustic wave in the liquid, generated by a suitable sound generator (speaker), for example an ultrasonic transducer.

The liquid is necessarily volatile, since it is an aerosolizable substrate material intended to be vaporized. This enables a further alternative, using thermal techniques, to generate the required pressure increase in the outlet tube.

Figure 7:
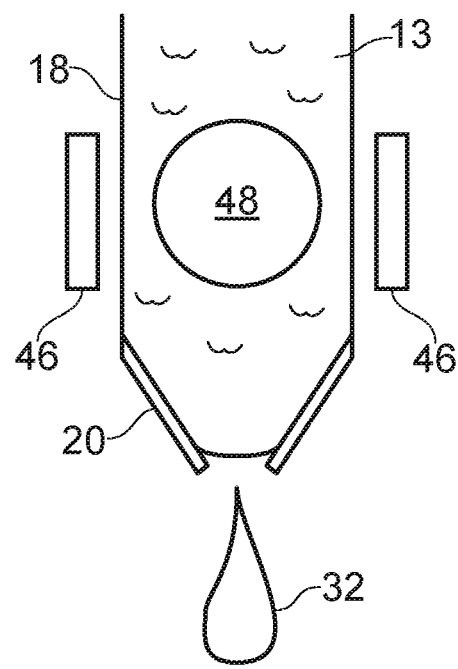
Figure 8:
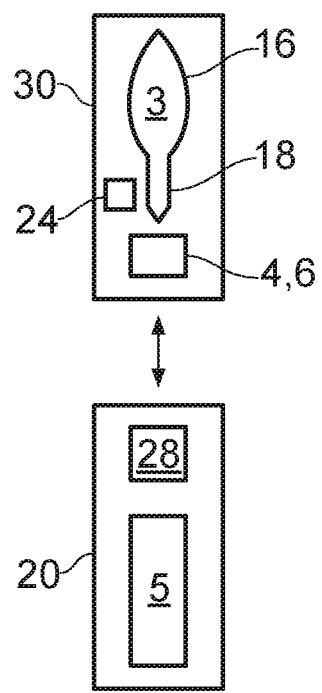
Figure 9:
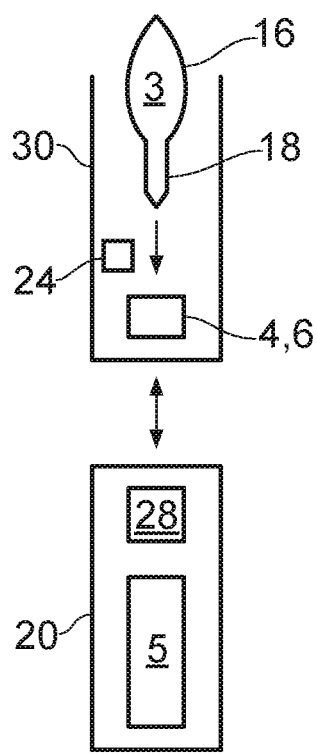
Figure 10:
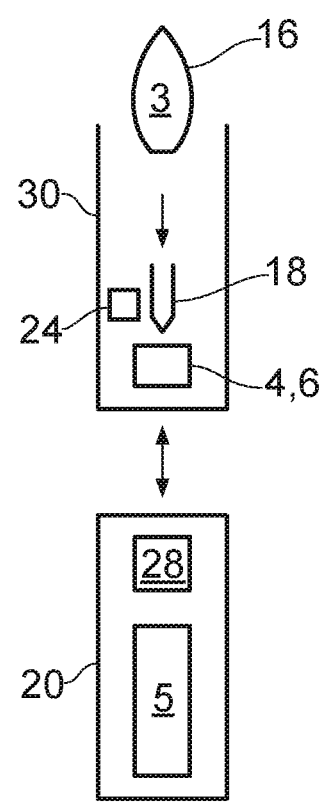

FIG. 7 shows a simplified cross-sectional view of an example utilizing a thermal effect. As before, the reservoir terminates in an outlet volume embodied as an outlet tube 18, with a one-way outlet valve 20 at its lower end remote from the storage volume of the reservoir (not shown). In this example, one or more heaters 46 (heating elements) are located adjacent to the wall of the tube. When liquid dispensing is required, the heaters 46 are activated to cause rapid heating of the liquid 13 inside the tube 18. The temperature rise causes vaporization of the liquid, creating one or more aerosol or vapor bubbles 48 inside the tube. Since the vapor phase is less dense than the liquid phase, the bubble 48 occupies a larger volume than the original liquid from which it was formed. This causes a pressure increase in the remaining liquid around the bubble, including liquid adjacent to the outlet valve 20. The higher pressure exceeds the cracking pressure of the valve 20, which opens and dispenses a liquid droplet 32.

The heaters may be electrically resistive elements, so that passing a pulse of current through them causes the required heating effect. The heaters may or may not be in contact with the wall of the outlet tube; a contacting heater will enable a quicker transfer energy from the heater to the liquid, however. The rate of transfer will be further enhanced if the tube is made from a material with efficient thermal conductivity properties. The heaters may be two or more separate heaters disposed around the tube, or may be one or more ring-shaped heaters that surround the tube. The heaters may be physically separate from the tube, and placed in contact or near-contact with the tube when the reservoir and the dispensing arrangement are assembled together. Alternatively, if the heaters are in thermal contact with the tube, they may be fixed to the outer surface of the tube wall to be an integral part of the reservoir, with the required electrical contact being made when the reservoir is coupled with the e-cigarette. The heaters may be affixed to the tube with a thermally conductive adhesive or cement, for example. Alternatively, the heaters may be thin film structures or traces deposited or printed onto the tube surface. In a further alternative, the heaters and the outlet tube may be combined as a single assembly, to which the storage volume part of the reservoir can be coupled or connected by the user, as already described. In some configurations, the heaters may be fabricated inside a chamber intended as the outlet tube, with both the chamber and the heaters formed using photolithography fabrication techniques. The reducible storage volume of the reservoir can then be connected to the chamber. Inductive heating techniques may be used instead of resistive heating.

Both the pressure wave dispensing technique and the thermal dispensing technique are similar to methods employed to eject ink droplets in inkjet printers.

The examples described above have included an outlet tube to define an outlet volume for the reservoir. Other shapes and configurations can be used to provide an outlet volume, however. The outlet volume is a part of the overall reservoir capacity containing a quantity of the liquid which experiences the pressure increase caused by the dispensing arrangement. Typically, this will be adjacent, immediately adjacent, or in the vicinity of the one-way outlet valve, so that the pressure increase is communicated quickly to cause the valve to open for dispensing. The outlet volume is in fluid communication with the storage volume part of the reservoir, which is bounded as least in part by the movable or collapsible wall which enables the volume to be reduced. The outlet volume may or may not be separated from the storage volume by a further one-way valve. The storage volume is remote from the outlet valve, with the outlet volume lying between the storage volume and the outlet valve. Accordingly, the reservoir can be configured with any shape or size of both the outlet volume and the storage volume that enables this arrangement.

Typically, the dispensing arrangement will require electrical power to produce the required movement or heating. Accordingly, the relevant parts of the dispensing arrangement are provided with power from a battery in the e-cigarette, such as battery 5 in FIG. 1. The supply of power can be under the control of a controller, such as controller 28 in FIG. 1. Operation of the e-cigarette can be activated by a user operating a switch, or by detection of a user inhalation on the e-cigarette, and in response, the controller provides power to the dispensing arrangement in order to deliver a portion of aerosolizable source material to the atomizer for generation to an aerosol for inhalation. It should be appreciated that the dispensing arrangement may be configured to deliver a single droplet or multiple droplets (two or more) in response to each operation or activation of the e-cigarette, depending on the particular design.

As mentioned above, an electronic cigarette or other vapor provision device may be a unitary device, or may be comprised of two or more separate components that can be coupled together for use by the user, typically to allow user choice and/or to allow replacement of rapidly consumed parts in combination with re-use of more long-term parts. For example, a cartridge or cartomizer consumable component containing the aerosolizable substrate material may be disposable when the substrate material is used up, and used in engagement with a control or power component or device that contains the battery and controller, which are intended for long-term use with multiple consumable components. The parts of the atomizer, including the vapor generator and any liquid transport element such as a wick, can be integral with the reservoir of aerosolizable substrate material, so as to be replicable with the reservoir, in a consumable component. In other designs, one or more parts of the atomizer may be reusable, so that only the reservoir requires replacement when the substrate material is used up.

Consequently, the various parts of the liquid dispensing concept described herein may be distributed in a range of ways between components that are connectable to make a complete vapor provision system.

A vapor provision system may be a unitary device and comprise a reducible volume reservoir with a dispensing arrangement. The system may be disposable when the reservoir is empty, or the reservoir may be refillable.

A cartridge, cartomizer or similar component may be connectable to a power and/or control component or device to make a vapor provision system, and comprise a reducible volume reservoir and a dispensing arrangement. The cartridge/cartomizer may be a consumable component to be disposed of once the reservoir is empty, or the reservoir may be refillable one or more times.

A cartridge, cartomizer or similar component may be connectable to a power and/or control component or device to make a vapor provision system, and comprise a reducible volume reservoir. The dispensing arrangement may be comprised in the power component.

A reducible volume reservoir may be a replaceable consumable, and a cartridge/cartomizer component, or a power/control component, or a unitary vapor provision system may comprise a dispensing arrangement with which the reservoir can be engaged for use. Further, the reservoir may be replaceable into the cartridge/cartomizer component, and the dispensing arrangement may be comprised in the power/control component, with the reservoir and the dispensing arrangement brought into engagement when the cartridge component and the power component are connected for use.

As noted above, the storage volume part of the reservoir might be separate from and connectable to the outlet volume part. Therefore, in some examples, the reservoir storage volume may be a replacement component, and the outlet volume part may form part of a common assembly with the dispensing arrangement. The common assembly might be housed in a cartridge component or a power component, with the reservoir to be fitted into the cartridge component.

FIGS. 8, 9 and 10 show simplified schematic representations (in which only relevant parts are depicted) of some of these example configurations, in which the reservoir has a collapsible pouch as its storage volume (as an example only; other reservoir configurations may be used). In FIG. 8, the vapor provision system comprises a power unit or device 20 with a battery 5 and a controller 28 which is separably connectable to a cartomizer or cartridge component (or similar) 30 which houses the reservoir 3 made up of the storage volume 16 and the outlet tube of the outlet volume 18, the adjacent dispensing arrangement 24, and the atomizer for example comprising a wick 6 and a heater 4, positioned to receive liquid portions dispensed from the outlet valve of the reservoir 3 by action of the dispensing arrangement 24.

FIG. 9 shows a system with a similar power unit 20 connectable to a cartomizer component 30 which includes a dispensing arrangement 24 and an atomizer 4, 6. A reducible volume reservoir 3 filled with liquid and formed of a storage volume 16 and an outlet volume 18 can be slotted into the cartomizer component 30 to bring the outlet volume into alignment for operation with the dispensing arrangement 24, so that liquid portions can be dispensed to the atomizer 4, 6.

In FIG. 10, the system has a similar power unit 24 connectable to a cartomizer component 30. In this example, the cartomizer component includes a dispensing arrangement 24 and an atomizer 4, 6, together with an outlet volume 18 for a reducible volume reservoir. The outlet volume 18 is adjacent to the dispensing arrangement so that the dispensing arrangement can operate on the dispensing arrangement to deliver liquid to the atomizer 4, 6. A reducible volume reservoir 3 comprising a storage volume 16 filled with liquid can be fitted into the cartomizer component 30 so that the storage volume engages into fluid communication with the outlet volume 18 to form a complete reservoir 3 and provide liquid for dispensing to the atomizer 4, 6.

In the above example vapor provision systems of FIGS. 8, 9 and 10, it is shown that the atomizer 4, 6 is located in the cartomizer component 30. However, this is not a required arrangement, and it should be understood that the atomizer 4, 6 (which may or may not include a wick or liquid transport element) may alternatively be provided in the power unit 20 and arranged so as to be in fluid communication with the outlet volume 18 when the cartomizer component 30 is coupled thereto. In addition, in some configurations the outlet volume 18 may also be located in the power unit 20.

Any of the example reservoir types described herein may be combined with any of the described examples of dispensing arrangement, and other configurations of reservoir and of dispensing arrangement which are in accordance with the appended claims may also be used in combination with each other or with any of the described examples.

Various types of valve may be employed as either or both of the one-way valves (outlet or distal valve 20, and the proximal valve 25 where included). Examples include burst valves, duck-bill valves, flap valves, ball bearing valves, umbrella valves, diaphragm valves, swing valves and tilting valves. Other types of valve are not excluded, however. In designs employing both a distal valve and a proximal valve, for example as shown in FIG. 5, the two valves may be the same type of valve or may be two different types.

In conclusion, in order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein. The disclosure may include other inventions not presently claimed, but which may be claimed in future.

The invention claimed is:

1. A component for a vapor provision system, comprising:
a reservoir for storing aerosolizable substrate material, the reservoir bounded by a boundary wall with at least one movable section configured to move to reduce a storage volume of the reservoir;
an outlet in the reservoir for dispensing aerosolizable substrate material from the reservoir;
a one-way outlet valve at the outlet configured to open for dispensing the aerosolizable substrate material; and
a dispensing arrangement operable to increase pressure of aerosolizable substrate material in an outlet volume of the reservoir which is not bounded by the movable section, so as to open the outlet valve and dispense a portion of the aerosolizable substrate material, the subsequent absence of the dispensed portion reducing the pressure to allow the movable section of the boundary wall to move to reduce the storage volume.

2. A component according to claim 1, wherein the dispensing arrangement comprises at least one element movable between a first position in which the element presses against a wall of the outlet volume to inwardly distort the wall and compress the aerosolizable substrate material in the outlet volume to increase the pressure, and a second position in which the element does not distort the wall.

3. A component according to claim 2, wherein the second position is a rest position of the element, the element moving to the first position when dispensing of a portion of the aerosolizable substrate material is required, and returning to the second position when the portion has been dispensed.

4. A component according to claim 2, wherein the first position is a rest position of the element, the element moving to the second position and back to the first position when dispensing of a portion of the aerosolizable substrate material is required.

5. A component according to claim 4, wherein, in the first position, the element presses the wall of the outlet volume so as to substantially close a bore defined in the outlet volume, thereby sealing the reservoir behind the one-way valve.

6. A component according to claim 1, wherein the dispensing arrangement comprises at least one heating element operable to heat aerosolizable substrate material in the outlet volume to create a bubble of vaporized aerosolizable substrate material which compresses unvaporized aerosolizable substrate material in the outlet volume to increase the pressure.

7. A component according to claim 1, wherein the dispensing arrangement comprises an impacting element operable to strike a wall of the outlet volume and generate a pressure wave in the aerosolizable substrate material in the outlet volume to increase the pressure.

8. A component according to claim 1, wherein the outlet volume is defined by a tube in fluid communication with the storage volume of the reservoir at a proximal end and having the outlet valve at a distal end.

9. A component according to claim 1, wherein a first pressure F1 required to open the outlet valve for the dispensing of the aerosolizable substrate material is less than a second pressure F2 required to open the outlet valve contrary to a one-way direction of the outlet valve and less than a third pressure F3 required to move the movable section of the boundary wall to reduce the storage volume, and the third pressure is less than the second pressure, such that $F1<F3<F2$.

10. A component according to claim 1, further comprising a one-way proximal valve between the storage volume and the outlet volume through which aerosolizable substrate material can move from the storage volume to the outlet volume.

11. A component according to claim 10, wherein a first pressure F1 is a pressure required to open the outlet valve for the dispensing of the aerosolizable substrate material, a second pressure F2 is a pressure required to open the outlet valve contrary to a one-way direction of the outlet valve, a fourth pressure F4 is a pressure required to open the proximal valve for movement of aerosolizable substrate material from the storage volume to the outlet volume, a fifth pressure F5 is a pressure required to open the proximal valve contrary to a one-way direction of the proximal valve, and the first pressure is less than the fifth pressure, $F1<F5$, and the fourth pressure is less than the second pressure, $F4<F2$.

12. A component according to claim 1, wherein the storage volume is defined by a circular or non-circular tubular boundary wall within which a plunger element is slidable along the axial dimension of the boundary wall to provide the movable section.

13. A component according to claim 12, wherein the outlet volume is at an opposite end of the storage volume to the plunger element, such that movement of the plunger element to reduce the storage volume is movement towards the outlet volume.

14. A component according to claim 13, wherein the storage volume comprises a pouch of flexible material that provides the boundary wall and the at least one movable section.

15. A component according to claim 1, further comprising a vapor generating element that receives aerosolizable substrate material dispensed from the reservoir and generate vapor therefrom.

16. A component according to claim 1, wherein the component is separably connectable to a power component comprising a battery to provide power to operate the dispensing arrangement.

17. An electronic vapor provision system comprising the component according to claim 1.

18. A reservoir installable into a vapor provision system and for storing aerosolizable substrate material, the reservoir comprising:
- a boundary wall defining a storage volume of the reservoir and having at least one movable section configured to reduce the storage volume; and
- an outlet volume in fluid communication with the storage volume, and which is not bounded by the movable section, the outlet volume having an outlet for dispensing aerosolizable substrate material from the reservoir and a one-way outlet valve at the outlet configured to open for the dispensing of the aerosolizable substrate material;
- wherein the outlet volume is configured to cooperate with a dispensing arrangement in a vapor provision system when the reservoir is installed in the vapor provision system, the dispensing arrangement operable to increase pressure of the aerosolizable substrate material in the outlet volume so as to open the outlet valve and dispense a portion of the aerosolizable substrate material, the subsequent absence of the dispensed portion reducing the pressure to allow the movable section of the boundary wall to move to reduce the storage volume.

19. A component for a vapor provision system, the component configured to receive a reservoir for storing aerosolizable substrate material that comprises a boundary wall defining a storage volume of the reservoir and having at least one movable section configured to reduce the storage volume, and an outlet volume not bounded by the movable section and in fluid communication with the storage volume, the outlet volume having an outlet for dispensing aerosolizable substrate material from the reservoir and a one-way outlet valve at the outlet configured to open for the dispensing of the aerosolizable substrate material;
- the component comprising a dispensing arrangement configured to cooperate with the outlet volume of a reservoir received by the vapor provision system, and operable to increase pressure of aerosolizable substrate material in the outlet volume so as to open the outlet valve and dispense a portion of aerosolizable substrate material, the subsequent absence of the dispensed portion reducing the pressure to allow the movable section of the boundary wall to move to reduce the storage volume.

20. A component for an aerosol provision device comprising:
- a reservoir for storing aerosolizable substrate material, the reservoir bounded by a boundary wall with at least one movable section configured to move to reduce a storage volume of the reservoir,
- an outlet in the reservoir for dispensing aerosolizable substrate material from the reservoir;
- a one-way valve at the outlet configured to open to enable the dispensing of aerosolizable substrate material; and
- a dispensing element configured to removably apply a force to the aerosolizable substrate material in an outlet volume of the reservoir which is not bounded by the movable section such that an application of the force by the dispensing element pushes a portion of aerosolizable substrate material through the one-way valve and the outlet, and subsequent removal of the force allows the movable section of the boundary wall to move to reduce the storage volume in response to the absence of the dispensed portion of the aerosolizable substrate material.

* * * * *